(12) United States Patent
Kuo et al.

(10) Patent No.: US 7,947,278 B2
(45) Date of Patent: May 24, 2011

(54) METHODS OF MODULATING ANGIOGENESIS

(75) Inventors: Calvin Jay Kuo, Palo Alto, CA (US); Frank Kuhnert, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 64 days.

(21) Appl. No.: 11/879,655

(22) Filed: Jul. 17, 2007

(65) Prior Publication Data

US 2008/0113911 A1     May 15, 2008

Related U.S. Application Data

(60) Provisional application No. 60/831,515, filed on Jul. 17, 2006.

(51) Int. Cl.
| | |
|---|---|
| *A61K 39/38* | (2006.01) |
| *A61K 31/00* | (2006.01) |
| *A61K 38/00* | (2006.01) |
| *A01N 61/00* | (2006.01) |
| *A01N 37/18* | (2006.01) |

(52) U.S. Cl. .............................. 424/184.1; 514/1; 514/2

(58) Field of Classification Search .................... None
See application file for complete search history.

(56) References Cited

U.S. PATENT DOCUMENTS

| 5,318,957 A | 6/1994 | Cid et al. |
|---|---|---|
| 2005/0059093 A1 * | 3/2005 | Bodmer et al. ................ 435/7.2 |
| 2007/0031437 A1 | 2/2007 | Filvaroff et al. |

FOREIGN PATENT DOCUMENTS

| WO | WO0102563 A2 | 1/2001 |
|---|---|---|
| WO | WO2004076482 A1 | 9/2004 |
| WO | WO 2005/117968 | * 12/2005 |

OTHER PUBLICATIONS

Campagnolo et al., "EGFL7 is a chemoattractant for endothelial cells and is up-regulated in angiogenesis and arterial injury," Am J Pathol., 2005, 167(1):275-284.
Fitch et al., "Egfl7, a novel epidermal growth factor-domain gene expressed in endothelial cells," Dev. Dyn., 2004, 230(2):316-324.
Parker et al., "The endothelial-cell-derived secreted factor Egfl7 regulates vascular tube formation," Nature, 2004, 428(6984):754-758.
Soncin, "VE-statin, an endothelial repressor of smooth muscle cell migration," Embo J., 2003, 22:5700-5711.

* cited by examiner

*Primary Examiner* — Alana M Harris
(74) *Attorney, Agent, or Firm* — Bozicevic, Field & Francis LLP; Pamela J. Sherwood

(57) ABSTRACT

The present invention provides methods of modulating angiogenesis in an individual, the methods generally involving administering to an individual an agent that modulates the expression or activity of Egfl7, where an agonist of Egfl7, including an Egfl7 polypeptide, decreases angiogenesis. In one embodiment, the methods of the invention relate to inhibiting pathological angiogenesis by enhancing activity of Egfl7, which method may be carried out in conjunction with administration of one or more other anti-angiogenic agents.

4 Claims, 8 Drawing Sheets

(5 of 8 Drawing Sheet(s) Filed in Color)

METHODS OF MODULATING ANGIOGENESIS

CROSS-REFERENCE TO RELATED APPLICATIONS

This application claims the benefit of priority to provisional application 60/831,515, filed Jul. 17, 2006, which is incorporated herewith by reference.

This invention was made with Government support under contract NIH-1R01CA95654-01 awarded by the National Institutes of Health. The Government has certain rights in this invention.

BACKGROUND OF THE INVENTION

Angiogenesis and vasculogenesis are processes involved in the growth of blood vessels. Angiogenesis is the process by which new blood vessels are formed from extant capillaries, while vasculogenesis involves the growth of vessels deriving from endothelial progenitor cells. Angiogenesis is a complex, combinatorial process that is regulated by a balance between pro- and anti-angiogenic molecules. Angiogenic stimuli (e.g. hypoxia or inflammatory cytokines) result in the induced expression and release of angiogenic growth factors such as vascular endothelial growth factor (VEGF) or fibroblast growth factor (FGF). These growth factors stimulate endothelial cells (EC) in the existing vasculature to proliferate and migrate through the tissue to form new endothelialized channels.

Angiogenesis and vasculogenesis, and the factors that regulate these processes, are important in embryonic development, inflammation, and wound healing, and also contribute to pathologic conditions such as tumor growth, diabetic retinopathy, rheumatoid arthritis; and chronic inflammatory diseases (see, e.g., U.S. Pat. No. 5,318,957; Yancopoulos et al. (1998) *Cell* 93:661-4; Folkman et al. (1996) *Cell* 87;1153-5; and Hanahan et al. (1996) *Cell* 86:353-64).

Both angiogenesis and vasculogenesis involve the proliferation of endothelial cells. Endothelial cells line the walls of blood vessels; capillaries are comprised almost entirely of endothelial cells. The angiogenic process involves not only increased endothelial cell proliferation, but also comprises a cascade of additional events, including protease secretion by endothelial cells, degradation of the basement membrane, migration through the surrounding matrix, proliferation, alignment, differentiation into tube-like structures, and synthesis of a new basement membrane. Vasculogenesis involves recruitment and differentiation of mesenchymal cells into angioblasts, which then differentiate into endothelial cells which then form de novo vessels (see, e.g., Folkman et al. (1996) *Cell* 87:1153-5).

Inappropriate, or pathological, angiogenesis is involved in the growth of atherosclerotic plaque, diabetic retinopathy, degenerative maculopathy, retrolental fibroplasia, idiopathic pulmonary fibrosis, acute adult respiratory distress syndrome, and asthma. Furthermore, tumor progression is associated with neovascularization, which provides a mechanism by which nutrients are delivered to the progressively growing tumor tissue.

While the concept of slowing or even halting the progression of cancer by targeting its blood supply was first proposed more than 30 years ago (Folkman, 1971), angiogenesis inhibitors are only now entering the mainstream of cancer therapeutics (Hurwitz et al., 2004). The success of Avastin, a monoclonal antibody raised against Vascular Endothelial Growth Factor (VEGF), in treating colon cancer brings hope for the use of angiogenesis inhibitors for the treatment of other malignancies such as prostate cancer—one of the most common cancers in men (Young, 2002). There is a need in the art for methods of reducing pathological angiogenesis. The present invention addresses this need.

Schuller et al. (1989) *Carcinogenesis* 10:1753-1755; Maneckjee et al. (1994) *Cell Growth Differ.* 5:1033-1040; Hong et al. (1995) *J. Pharm. Sci.* 84:65-70; Schuller et al. (1989) *Biochem. Pharmacol.* 38:3439-3442; U.S. Pat. No. 5,318,957; Yancopoulos et al. (1998) *Cell* 93:661-4; Folkman et al. (1996) *Cell* 87;1153-5; and Hanahan et al. (1996) *Cell* 86:353-64). Carmeliet et al. (2000) *Nature* 407:249-257; Folkman (1995) *Nat Med* 1:27-31; Heeschen et al. (2001) *Nat Med* 7:833-837; Grando et al. (1995) *J Invest Dermatol* 105:774-781; Macklin et al. (1998) *Pharmacol Exp Ther* 287:435-439; Wessler et al. (1999) *Clin Exp Pharmacol Physiol* 26:198-205; Kawashima et al. (1989) *Neurosci Lett* 104:336-339; Kawashima et al. (1990) *Neurosci Lett* 119:156-158; Kureishi et al. (2000) *Nat Med* 6:1004-1010; Jang et al. (2000) *Circulation* 102:1414-1419; Couffinhal et al. (1998) *Am J Pathol* 152:1667-1679; Lagasse and Weissman (1996) *J Immunol Methods* 197:139-150; and Villablanca (1998 *J Appl Physiol* 84:2089-2098.

SUMMARY OF THE INVENTION

The present invention provides methods of reducing angiogenesis in an individual. The methods generally involve administering to the individual an effective amount of an Egfl7 agonist, which agonists may include Eglf7 polypeptides. The methods are useful to treat conditions associated with or resulting from angiogenesis, particularly pathological angiogenesis. The invention further provides methods of treating a condition associated with or resulting from angiogenesis.

The present invention features a method of reducing angiogenesis in a mammal. The method generally involves administering to a mammal an Egfl7 agonist in an amount effective to reduce angiogenesis. It is shown herein that Egfl7 acts to inhibit the migration and tube formation by endothelial cells.

The present invention also features method of treating a disorder associated with pathological angiogenesis. In some embodiments, the invention features a method of inhibiting abnormal fibrovascular growth in a mammal. In some of these embodiments, the abnormal fibrovascular growth is associated with inflammatory arthritis. In some embodiments, the invention features a method of inhibiting a proliferative retinopathy in a mammal. In some of these embodiments, the proliferative retinopathy occurs as a result of diabetes in the mammal. The methods generally involve administering to a mammal an Egfl7 agonist in an amount effective to reduce pathological angiogenesis. In some embodiments, the methods further comprise administering a second angiogenesis inhibitor.

The present invention further features a method of inhibiting tumor growth in a mammal. In some embodiments, the invention features a method of inhibiting pathological neovascularization associated with a tumor. The methods generally involve administering to a mammal an Egfl7 agonist in an amount effective to reduce angiogenesis associated with a tumor. In some embodiments, the invention further comprises administering an anti-tumor chemotherapeutic agent other than an Egfl7 agonist.

BRIEF DESCRIPTION OF THE DRAWINGS

The patent or application file contains at least one drawing executed in color. Copies of this patent application publication with color drawing(s) will be provided by the U.S. Patent and Trademark Office upon request and payment of the necessary fee.

DEFINITIONS

Figure 1:
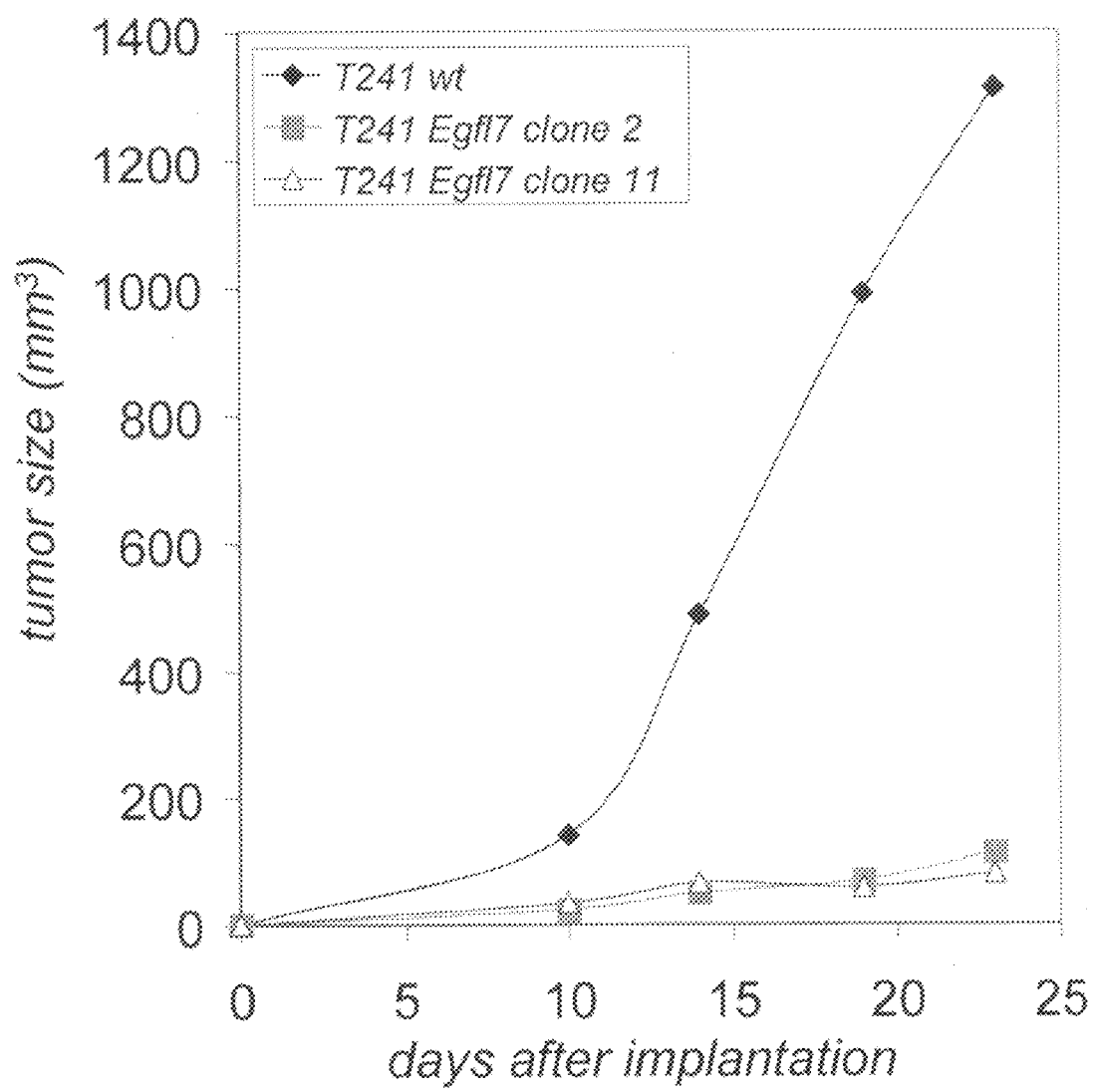
FIG. 1. Effect of angiogenesis inhibition on tumor growth and survival.
Figure 2:
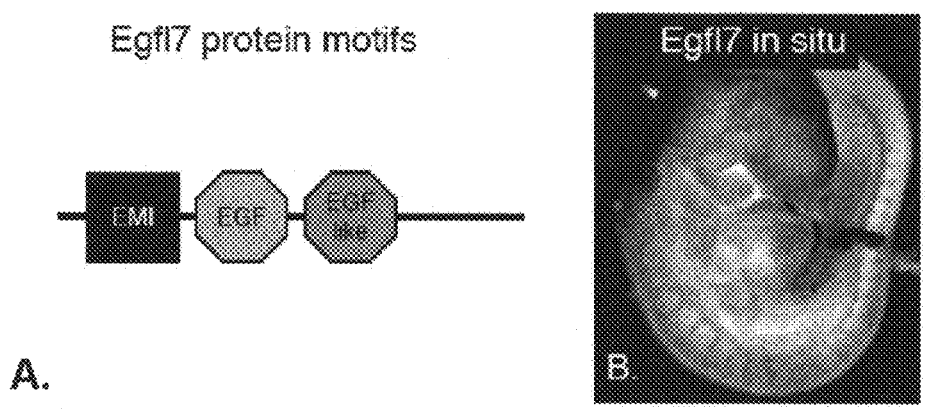
FIGS. 2A-2B show Egfl7 structural motifs and expression pattern.

Egfl7 is a 30 kDa highly conserved endothelial cell-secreted protein containing a signal peptide, two EGF repeats, and a cysteine-rich EMI domain (FIG. 2). Egfl7 is secreted but tightly associated with the extracellular matrix, rendering purification of soluble active protein problematic. During embryonic development, Egfl7 is clearly expressed in a pan-endothelial fashion with strong expression in all vascular beds (FIG. 2), while it is largely absent in resting adult vasculature.

The terms "treatment", "treating" and the like are used herein to generally mean obtaining a desired pharmacologic and/or physiologic effect, e.g., reduction of angiogenesis and/or vasculogenesis. The effect may be prophylactic in terms of completely or partially preventing a disease or symptom thereof and/or may be therapeutic in terms of a partial or complete cure for a disease and/or adverse effect. "Treatment" as used herein covers any treatment of a disease in a mammal, particularly a human, and includes: (a) preventing a disease or condition from occurring in a subject who may be predisposed to the disease but has not yet been diagnosed as having it; (b) inhibiting the disease, e.g., arresting its development; or (c) relieving the disease. In the context of the present invention, reduction of angiogenesis and/or vasculogenesis is employed for subject having a disease or condition amenable to treatment by reducing angiogenesis.

By "therapeutically effective amount of an Egfl7 agonist" is meant an amount of an Egfl7 agonist effective to facilitate a desired therapeutic effect, e.g., a desired reduction of angiogenesis and/or vasculogenesis. The precise desired therapeutic effect will vary according to the condition to be treated.

Included in the term "Egfl7 agonist" is an active Egfl7 polypeptide. EGFL7 peptides, which can be used in the methods of the invention, comprise at least about 10 amino acids, usually at least about 12 amino acids, at least about 15 amino acids, and which may include up to or more than 50 amino acids of a EGFL7 peptide, including domains and larger fragments of about 100 amino acids or more; and modifications thereof, and may further include fusion polypeptides as known in the art in addition to the provided sequences. A combination of one or more forms may be used. The EGFL7 sequence may be from any mammalian or avian species, e.g. primate sp., particularly humans; rodents, including mice, rats and hamsters; rabbits; equines, bovines, canines, felines; etc. Of particular interest are the human proteins.

There are two splice variants of the human Egfl7 protein (also referred to as VE-statin), both of which encode a deduced 273-amino acid protein with a calculated molecular mass of 29.6 kD (see Soncin, et al. (2003) *EMBO J.* 22: 5700-5711, herein incorporated by reference). The mouse and human EGFL7 proteins both contain an N-terminal cleavable signal peptide followed by 2 epidermal growth factor-like domains, and they share 78% amino acid identity. The mouse Egfl7 is a deduced 278-amino acid protein with a calculated molecular mass of 29 kD.

Functional variants of the EGFL7 polypeptide are of interest. Such variants may have substantial sequence similarity to a native EGFL7 sequence, for example SEQ ID NO:1, usually at least about 90% sequence identity; at least about 95% sequence identity; up to at least about 99% sequence identity or more. Such variants may comprise 1, 2, 3, 4, 5, or more amino acid substitutions, deletions or additions, including conservative substitutions.

Functional variants may also be assessed by the ability of a variant to activate pathways mediated by the wild-type EGFL7 polypeptide, for example where the variant has an activity at least equal to the wild-type protein; and activity greater than the wild-type protein; or an activity not less than about 25% the activity of the wild-type protein. The activity may be ligand dependent or ligand independent, usually ligand dependent.

EGFL7 has been identified as having certain activities, as reported herein, in the inhibition of angiogenesis, and such assays may be performed according to the examples set forth herein to determine activity of an Egfl7 variant.

By "isolated" is meant that the compound is separated from all or some of the components that accompany it in nature.

By "substantially pure Egfl7 agonist" is meant that the Egfl7 agonist has been separated from components that accompany it in nature. Typically, an Egfl7 agonist is substantially pure when it is at least 60%, by weight, free from naturally-occurring organic molecules with which it is naturally associated. Preferably, the preparation is at least 75%, more preferably at least 90%, and most preferably at least 99%, by weight, Egfl7 agonist. A substantially pure Egfl7 agonist can be obtained, for example, by extraction from a natural source, by recombinant synthesis, by chemically synthesizing the compound, or by a combination of purification and chemical modification. Purity can be measured by any appropriate method, e.g., chromatography, mass spectroscopy, HPLC analysis, etc.

An Egfl7 agonist is substantially free of naturally associated components when it is separated from those contaminants which accompany it in its natural state. Thus, e.g., an Egfl7 agonist which is chemically synthesized or produced in a cellular system different from the cell from which it naturally originates will be substantially free from its naturally associated components. In many embodiments, e.g., where an Egfl7 agonist is chemically synthesized, the Egfl7 agonist is generally substantially pure, e.g., at least about 90% pure, at least about 95% pure, or at least about 99% pure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an Egfl7 agonist" includes a plurality of such antagonists and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of reducing angiogenesis in an individual. The methods generally involve administering to an individual an effective amount of a Egfl7 agonist. The methods are useful to treat conditions and disorders associated with or resulting from angiogenesis, particularly pathological angiogenesis.

The results presented herein indicate that Egfl7 agonists are useful to treat conditions and disorders associated with and/or resulting from pathological angiogenesis, including, e.g., cancer, atherosclerosis, proliferative retinopathies, excessive fibrovascular proliferation as seen with chronic arthritis, psoriasis, and vascular malformations such as hemangiomas.

The present invention provides methods of reducing angiogenesis in an individual. The methods generally involve administering to an individual an effective amount of an Egfl7 agonist. Egfl7 agonists can be identified using readily available methods, including those described in the Example. The ability of a candidate agent to reduce angiogenesis can be assessed in vitro or in vivo using any known method, including, but not limited to, an in vitro Matrigel assay, a disc angiogenesis system, a murine model of hind limb ischemia, a murine model of lung cancer, and the like.

Upon reading the present specification, the ordinarily skilled artisan will appreciate that the pharmaceutical compositions comprising an Egfl7 agonist described herein can be provided in a wide variety of formulations. More particularly, the Egfl7 agonist can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols.

The Egfl7 agonist formulation used will vary according to the condition or disease to be treated, the route of administration, the amount of Egfl7 agonist to be administered, and other variables that will be readily appreciated by the ordinarily skilled artisan. In general, and as discussed in more detail below, administration of Egfl7 agonists can be either systemic or local, and can be achieved in various ways, including, but not necessarily limited to, administration by a route that is oral, parenteral, intravenous, intra-arterial, interpericardial, intramuscular, intraperitoneal, intra-articular, intra-ocular, topical, transdermal, transcutaneous, subdermal, intradermal, intrapulmonary, etc.

In pharmaceutical dosage forms, the Egfl7 agonist may be administered in the form of their pharmaceutically acceptable salts, or they may also be used alone or in appropriate association, as well as in combination, with other pharmaceutically active compounds. The following methods and excipients are merely exemplary and are in no way limiting.

The Egfl7 agonist can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Formulations suitable for topical, transcutaneous, and transdermal administration may be similarly prepared through use of appropriate suspending agents, solubilizers, thickening agents, stabilizers, and preservatives. Topical formulations may be also utilized with a means to provide continuous administration, for example, incorporation into slow-release pellets or controlled-release patches.

The Egfl7 agonist can also be formulated in a biocompatible gel, which gel can be applied topically or implanted (e.g., to provide for sustained release of Egfl7 agonist at an internal treatment site). Suitable gels and methods for formulating a desired compound for delivery using the gel are well known in the art (see, e.g., U.S. Pat. Nos. 5,801,033; 5,827,937; 5,700,848; and MATRIGEL™).

For oral preparations, the Egfl7 agonist can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The Egfl7 agonist can be utilized in aerosol formulation to be administered via inhalation. The compounds of the present invention can be formulated into pressurized acceptable propellants such as dichlorodifluoromethane, propane, nitrogen and the like.

Furthermore, the Egfl7 agonist can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term unit dosage form, as used herein, refers to physically discrete units suitable as unitary dosages for human and/or animal subjects, each unit containing a predetermined quantity of Egfl7 agonist calculated in an amount sufficient to produce the desired reduction in angiogenesis in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an Egfl7 agonist is administered in a combination therapy with one or more additional therapeutic agents. Exemplary therapeutic agents include therapeutic agents used to treat cancer, atherosclerosis, proliferative retinopathies, chronic arthritis, psoriasis, hemangiomas, etc.

Dose

The dose of Egfl7 agonist administered to a subject, particularly a human, in the context of the present invention should be sufficient to effect a therapeutic reduction in angiogenesis in the subject over a reasonable time frame. The dose will be determined by, among other considerations, the potency of the particular Egfl7 agonist employed and the condition of the subject, as well as the body weight of the subject to be treated. The size of the dose also will be determined by the existence, nature, and extent of any adverse side-effects that might accompany the administration of a particular compound.

In determining the effective amount of Egfl7 agonist in the reduction of angiogenesis, the route of administration, the kinetics of the release system (e.g., pill, gel or other matrix), and the potency of the agonist are considered so as to achieve the desired anti-angiogenic effect with minimal adverse side effects. The Egfl7 agonist will typically be administered to the subject being treated for a time period ranging from a day to a few weeks, consistent with the clinical condition of the treated subject.

As will be readily apparent to the ordinarily skilled artisan, the dosage is adjusted for Egfl7 agonist according to their potency and/or efficacy relative to a standard, e.g., native Egfl7 protein. A dose may be in the range of about 0.01 µg to 10 mg, given 1 to 20 times daily, and can be up to a total daily dose of about 0.1 µg to 100 mg. If applied topically, for the purpose of a systemic effect, the patch or cream would be designed to provide for systemic delivery of a dose in the range of about 0.01 µg to 10 mg. If injected for the purpose of a systemic effect, the matrix in which the Egfl7 agonist is administered is designed to provide for a systemic delivery of a dose in the range of about 0.001 µg to 1 mg. If injected for the purpose of a local effect, the matrix is designed to release locally an amount of Egfl7 agonist in the range of about 0.003 µg to 1 mg.

Regardless of the route of administration, the dose of Egfl7 agonist can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated.

Combination Therapy

In some embodiments, an Egfl7 agonist is administered in a combination therapy with one or more other therapeutic agents, including an inhibitor of angiogenesis; and a cancer chemotherapeutic agent.

Suitable chemotherapeutic agents include, but are not limited to, the alkylating agents, e.g. Cisplatin, Cyclophosphamide, Altretamine; the DNA strand-breakage agents, such as Bleomycin; DNA topoisomerase II inhibitors, including intercalators, such as Amsacrine, Dactinomycin, Daunorubicin, Doxorubicin, Idarubicin, and Mitoxantrone; the nonintercalating topoisomerase II inhibitors such as, Etoposide and Teniposide; the DNA minor groove binder Plicamycin; alkylating agents, including nitrogen mustards such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine; antimetabolites, including folate antagonists such as Methotrexate and trimetrexate; pyrimidine antagonists, such as Fluorouracil, Fluorodeoxyuridine, CB3717, Azacytidine, Cytarabine; Floxuridine purine antagonists including Mercaptopurine, 6-Thioguanine, Fludarabine, Pentostatin; sugar modified analogs include Cyctrabine, Fludarabine; ribonucleotide reductase inhibitors including hydroxyurea; Tubulin interactive agents including Vincristine Vinblastine, and Paclitaxel; adrenal corticosteroids such as Prednisone, Dexamethasone, Methylprednisolone, and Prodnisolone; hormonal blocking agents including estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; and the like.

The Egfl7 agonist may be administered with other anti-angiogenic agents. Anti-angiogenic agents include, but are not limited to, angiostatic steroids such as heparin derivatives and glucocorticosteroids; thrombospondin; cytokines such as IL-12; fumagillin and synthetic derivatives thereof, such as AGM 12470; interferon-α; endostatin; soluble growth factor receptors; neutralizing monoclonal antibodies directed against growth factors such as vascular endothelial growth factor; and the like.

Reducing Angiogenesis in Vivo

The instant invention provides a method of reducing angiogenesis in a mammal. The method generally involves administering to a mammal an Egfl7 agonist in an amount effective to reduce angiogenesis. An effective amount of an Egfl7 agonist reduces angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or more, when compared to an untreated (e.g., a placebo-treated) control.

Whether angiogenesis is reduced can be determined using any known method. Methods of determining an effect of an agent on angiogenesis are known in the art and include, but are not limited to, inhibition of neovascularization into implants impregnated with an angiogenic factor; inhibition of blood vessel growth in the cornea or anterior eye chamber; inhibition of endothelial cell proliferation, migration or tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

Conditions Amenable to Treatment

Any condition or disorder that is associated with or that results from pathological angiogenesis, or that is facilitated by neovascularization (e.g., a tumor that is dependent upon neovascularization), is amenable to treatment with an Egfl7 agonist.

Conditions and disorders amenable to treatment include, but are not limited to, cancer; atherosclerosis; proliferative retinopathies such as diabetic retinopathy, age-related maculopathy, retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

In some embodiments, an agent that agonizes Egfl7-regulated gene is a small molecule, e.g., a small organic or inorganic compound having a molecular weight of more than about 50 daltons and less than about 20,000 daltons, e.g., from about 50 daltons to about 100 daltons, from about 100 daltons to about 200 daltons, from about 200 daltons to about 500 daltons, from about 500 daltons to about 1000 daltons, from about 1000 daltons to about 2500 daltons, from about 2500 daltons to about 5000 daltons, from about 5000 daltons to about 7,500 daltons, from about 7,500 daltons to about 10,000 daltons, from about 10,000 daltons to about 15,000 daltons, or from about 15,000 daltons to about 20,000 daltons. Agents may comprise functional groups necessary for structural interaction with proteins and/or nucleic acids, e.g., hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, an agent that agonizes Egfl7 gene is a nucleic acid, e.g., an antisense RNA, an interfering RNA (including short interfering RNA; "siRNA"), a ribozyme, and the like, usually a nucleic acid encoding an Egfl7 polypeptide, operably linked to a promoter active in the cells of interest.

An Egfl7 encoding polynucleotide sequence (e.g., cDNA or genomic DNA) may be inserted into a replicable vector for expression. Many such vectors are available. The vector components generally include, but are not limited to, one or more of the following: an origin of replication, one or more marker genes, an enhancer element, a promoter, and a transcription termination sequence.

Egfl7 polypeptides may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the Egfl7 polypeptide DNA that is inserted into the vector. The heterologous signal sequence selected preferably is one that is recognized and processed (i.e., cleaved by a signal peptidase) by the host cell. In mammalian cell expression the native signal sequence may be used, or other mammalian signal sequences may be suitable, such as signal sequences from other animal Egfl7 polypeptide, and signal sequences from secreted polypeptides of the same or related species, as well as viral secretory leaders, for example, the herpes simplex gD signal.

Expression vectors will contain a promoter that is recognized by the host organism and is operably linked to the Egfl7 coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native Egfl7 polypeptide promoter sequence and many heterologous promoters may be used to direct expression of a Egfl7 polypeptide. However, heterologous promoters are preferred, as they generally permit greater transcription and higher yields.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Particularly useful in the practice of this invention are expression vectors that provide for the transient expression in mammalian cells. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

In one embodiment, definition of optimal dose and treatment duration of the Egfl7 polypeptide in preclinical models may utilize an adenovirus technology (Ad TRE (Tetracycline response element)) which permits rigorously controlled expression of adenovirally carried transgenes under the control of the tetracycline operator/promoter system. Expression of the desired transgene engineered in the Ad TRE adenovirus utilizes co-infection with Ad tTA (tetracycline transactivator), which is an adenovirus which expresses the requisite transcription factor for the TRE system. In the absence of tetracycline (or its analog doxycycline), co-infection with Ad TRE and Ad tTA viruses results in expression of a desired transgene; the duration of expression can be precisely controlled by timed initiation of doxycycline treatment both in vitro and in vivo. The amplitude of the transgene product serum levels in vivo can be modulated by changing the Ad TRE dose, by varying the ratio of Ad TRE/Ad tTA, or by administering a titrated, low-dose of doxycycline to the experimental animals. For dosing in humans, recombinant Egfl7 validated in pre-clinical models are tested in dose-finding studies. Such assessment may include the pharmacokinetic properties, etc.

Stimulation of Therapeutic Angiogenesis

In some embodiments, a stimulator of therapeutic angiogenesis is administered to an individual in need thereof. In these embodiments, the stimulator of angiogenesis is an active agent that inhibits Egfl7 activity or expression, and increases angiogenesis. Thus, in some embodiments, the instant invention provides a method of increasing or stimulating angiogenesis in a mammal. The method generally involves administering to a mammal an active agent in an amount effective to inhibit Egfl7 activity, thereby increasing angiogenesis.

An effective amount of an Egfl7 inhibitor increases angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 2-fold, at least about 5-fold, at least about 10-fold, or more, when compared to an untreated (e.g., a placebo-treated) control. Stimulation of angiogenesis is useful to treat a variety of conditions that would benefit from stimulation of angiogenesis, stimulation of vasculogenesis, increased blood flow, and/or increased vascularity.

Examples of conditions and diseases amenable to treatment according to the method of the invention related to increasing angiogenesis include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Screening Assays

The present invention further provides methods of identifying an agent that modulates angiogenesis. The methods may involve contacting a cell that is responsive to Egfl7 with a test agent, for example in a competitive assay with Egfl7; and assessing the effect of the test agent upon Egfl7 mediated effects. Alternatively, an agonist or antagonist of Egfl7 may be designed to bind to or mimic the activity of Egfl7, e.g. in the design of a polypeptide or peptidomimetic agent. Such an agent may then be tested in any standard angiogenesis assay to confirm activity.

The terms "agent", "substance", and "compound" are used interchangeably herein, with the interchangeable terms "candidate agent," and "test agent" referring to agents used in screening assays to identify those having a desired activity in modulating angiogenesis according to the present invention. "Agents" encompass numerous biological and chemical classes, including synthetic, semi-synthetic, or naturally-occurring inorganic or organic molecules, including synthetic, recombinant or naturally-occurring polypeptides and nucleic acids (e.g., nucleic acids encoding a gene product, antisense RNA, siRNA, and the like). "Candidate agents" or "test agents" particularly include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

In general, agents of interest include small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents, particularly candidate agents, are also found among biomolecules including peptides, saccharides, fatty acids, steroids, purines, pyrimidines, derivatives, structural analogs or combinations thereof.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Anti-angiogenic therapy targeting not the tumor cells themselves but rather tumor blood vessels has demonstrated great promise in human cancer patients, most notably in a randomized phase III trial of the anti-VEGF monoclonal antibody Avastin in metastatic colorectal cancer. Despite the efficacy of VEGF blockade in animal models and humans, such treatment has been nevertheless characterized by progressive disease and largely modest survival improvements. Accordingly, we have exploited our adenoviral approach to greatly facilitate the search for novel anti-angiogenic compounds which could be either superior to VEGF blockade, or have additive/synergistic effects when combined with VEGF blockade.

The ease of adenoviral production versus recombinant protein, and the persistent high-level transgene expression following single i.v. virus injection has allowed us to rapidly screen over 30 potentially anti-angiogenic proteins in vivo, including ectodomains of the Tie2 and EphB4 endothelial receptor tyrosine kinases, and of the pericyte PDGFRβ receptor. Out of this initial screen, a factor designated Egfl7 was shown to have potent anti-angiogenic activity in vivo.

Egfl7 is a recently described secreted protein containing two EGF repeats which is expressed in a pan-endothelial fashion during mouse development; however, its potential anti-angiogenic properties in any tumor type, have not been examined.

In a screen of over 30 potentially novel anti-angiogenic proteins delivered by adenovirus, we have found that the secreted peptide Egfl7 (also known as VE-Statin) exhibits potent anti-angiogenic activity in vivo, leading to the use of Egfl7 for the treatment of prostate cancer and other vascular dependent diseases.

As shown in FIG. 2(A). Egfl7 is a 30 kDa highly conserved endothelial cell-secreted protein containing a signal peptide, a cysteine-rich EMI domain and two EGF repeats. (B). During development, Egfl7 is expressed in a panendothelial fashion with strong expression in all vascular beds.

Figure 3:
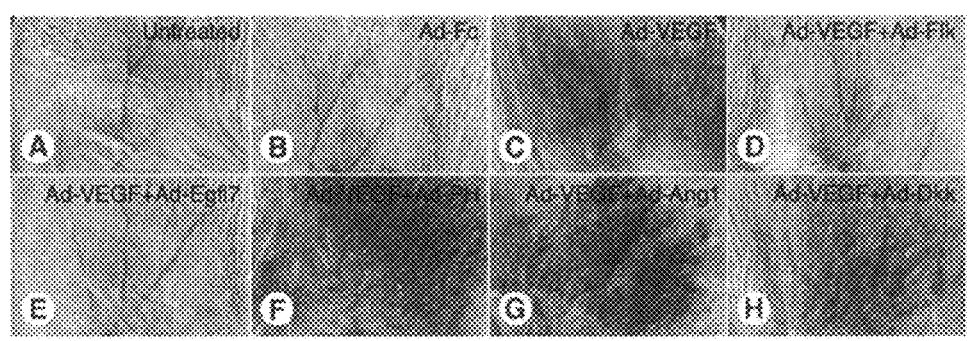
FIGS. 3A-3H show inhibition of in vivo angiogenesis by Egfl7.

As shown in FIG. 3, gross specimens of adult 129sV mouse ear that were either untreated (A) or treated with subcutaneous local injections of the negative control virus Ad-Fc (expressing an immunoglobulin IgG2(Fc fragment) (B), Ad-VEGF (C), or a combination of Ad-VEGF with either Ad-Flk1-Fc (expressing a Flk1-FcNEGFR2 soluble ectodomain) (D), Ad-Egfl7 (E), Ad-PDGFR□(Ad-PH, PDGFR□ectodomain), (F), Ad-Ang-1 (G), or Ad-Dkk1 (expressing the Wnt inhibitor Dickkopf-1, H). With the exception of a few large vessels, the vasculature of murine ear that is left untreated or treated with Ad-Fc is not visible through the skin (A, B). Upon treatment with Ad-VEGF, large red patches of vasculature are grossly visible through the ear skin (C). Treatment with Ad-Flk1-Fc, a well-characterized inhibitor of angiogenesis and, interestingly, Ad-Egfl7, both potently inhibit the VEGF induced changes in the vasculature (D, E). Similar results are not seen with other adenoviruses inhibiting the PDGF or Wnt pathways or encoding Ang-1 (F-H).

Figure 4:
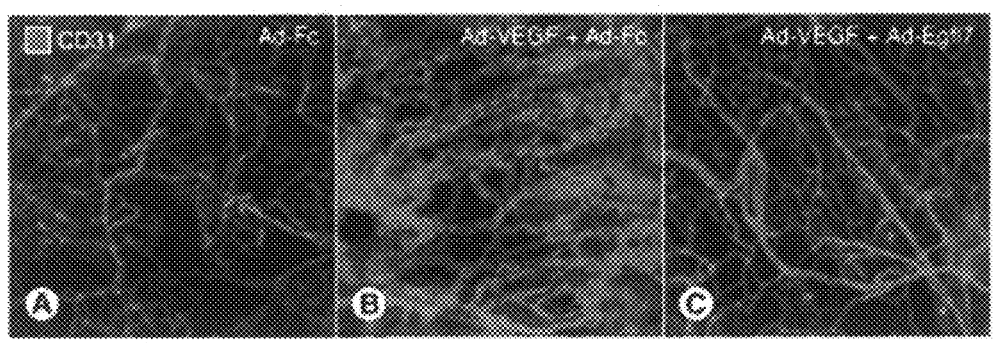
FIGS. 4A-4C show inhibition of angiogenesis by Egfl7.

Histologic analysis is described in FIG. 4. CD31 staining of whole mount preparations of murine ear three days after subcutaneous injection with adenovirus show the normal vascular patterning of the reticular dermis of the ear after treatment with control virus (A). As expected, treatment with Ad-VEGF induces robust cellular changes in the structural features of the blood vessels and increases vascularity (B). Strikingly, co-injection with Ad-Egfl7 results in the inhibition of these VEGF-induced changes in the vasculature (C).

Example 2

Materials and Methods creation of tumor cell lines that constitutively express Egfl7: Lentiviral constructs expressing Egfl7-IRES-GFP or IRES-GFP alone were created by cloning the Egfl7 cDNA tagged with 6× Histidine into the pHRST-IRES-GFP backbone. Lentiviruses were packaged in 293T cells by triple transfection with Lipofectamine 2000 (Invitrogen). T241 fibrosarcoma cells were infected with Egfl7 expressing viruses and GFP expressing, control viruses in minimal volume in the presence of 1× Polybrene. Transduced T241 cells were isolated by Fluorescence Activated Cell Sorting (FACS) at the Stanford University FACS core as GFP positive cells and plated at a density of 1 cell/100 µL in individual wells of a 96 well plates. Individual GFP positive clones were expanded and expression of the Egfl7 gene was confirmed by Western Blotting with a rabbit polyclonal anti-Egfl7 antibody.

Tumor Proliferation Assay: To exclude direct effects on tumor proliferation, the growth kinetics of T241 cells infected with either lentivirus Egfl7-IRES-GFP or IRES-GFP were monitored in tissue culture over a period of 5 days. In brief, tumor cells were plated at a density of 500 cells/well on five 24 well plates. One plate was harvested every 24 hours and stored at −80° C. All 5 plates were subsequently stained with 200 µL/well of CyQuant GR dye (excitation/emission maxima~480/530, Molecular Probes) and read in a Flexstation II 384 fluorescence microplate reader. The fluorescence unit of each well is directly proportional to the number of cells and represents the mean of 3 separate wells.

Tumor Implantation and Measurement: $2 \times 10^7$ T241 fibrosarcoma cells expressing Egfl7 or control GFP were resuspended in 2 mL 1× Phosphate Buffered Saline (PBS) for a cell concentration of $1 \times 10^6$ cells/100 µL on the day of the implantation. Mice were anesthetized with 1× Avertin and then injected subcutaneously with $1 \times 10^6$ cells (n=12 per group). Subcutaneous tumors were measured by calipers at least once a week for a period of about one month. Solid tumors were modeled as a prolate spheroid with a volume determined by the formula: $(4/3)*\therefore *(length/2)*(width/2)\hat{}2$ with length defined as the largest dimension.

Analysis of Tumor Vasculature: Mice having tumors around 100 cubic mm in volume were taken from each group to be perfused and analyzed by immunofluorescence. After anesthetization with 1× Avertin, mice were perfused systemically with 1% paraformaldehyde through the left ventricle for 2 minutes at a pressure of 120 mmHg. Fixed tumors were cryoembedded and sectioned to a thickness of 10 µm and stored at −80° C. Before antibody labeling, sectioned tumors were thawed at room temperature, permeabilized with 0.3% Triton X-100 in 1× PBS (TPBS) and blocked with 5% goat serum in TPBS. To visualize the vasculature, the tumors were then stained at 4° C. overnight with rat monoclonal anti-mouse CD31 (PECAM-1, clone MEC 13.3, 1:250 in 5% goat serum in TPBS, Pharmingen, San Diego, Calif.). The following day, the samples were washed with 1×PBS and then labeled with FITC conjugated goat anti-rat IgG (1:400 in 5% goat serum in TPBS, Jackson ImmunoResearch, West Grove, Pa.) for 4 hours in the dark. Unbound secondary antibodies were washed off by 1×PBS and samples were then fixed with 4% Paraformaldehyde and mounted for subsequent immunofluorescent visualization.

Assessment of Vascular Density Fluorescent digital pictures of tumor sections labeled with FITC conjugated anti-CD31 antibodies were analyzed using Volocity software (Improvision) and Adobe Photoshop (Adobe). Using Volocity's pixels having intensity greater than an established threshold were selected and counted. The total number of pixels in the picture was also determined using Adobe Photoshop's histogram tool. The percent vascular density of each picture can then be calculated by dividing the number of pixels that are above the threshold by the total number of pixels. The mean percent vascular density is plotted for 10 T241 GFP pictures and 8 T241 Egfl7 pictures. The difference in percent vascular density between the two groups was calculated using Student's t-test with an alpha of 0.05.

Costaining of Pericytes and Endothelial Cells Pericytes were visualized by labeling with a Cy3 conjugated mouse monoclonal anti-Smooth Muscle Actin antibody (clone 1A4, 1:500 in 5% goat serum in TPBS, Sigma Chemical Co., St. Louis, Mo.) overnight at 4° C. Endothelial cells were labeled as described before. Fluorescent images of Cy3 labeled pericytes and FITC labeled endothelial cells were overlaid using Adobe Photoshop.

Creation of HUVECs Expressing EGFL7: Passage 2 Human Umbilical Vein Endothelial Cells (HUVECs) were seeded for lentiviral infection at a density of $2.5 \times 10^5$ cells/well of a 6 well plate in 3 mL of EBM2-EGM2 media (Cambrex). On the day of the infection growth medium was replaced with 100 µL of concentrated Lentivirus expressing Egfl7 supplemented with 500 µL EBM2-EGM2 media and 0.6 µL 1000× Polybrene. A separate well was also infected with 300 µL unconcentrated Lentivirus expressing only GFP in 300 µL EBM2-EGM2 media with 0.6 µL 100× Polybrene. After six hours the infection media was diluted to 3 mL with EBM2-EGM2 media. The media was replaced after 24 hours and infection efficiency was determined by visualization of GFP positive cells 48 hours post-infection. Egfl7 expression was further confirmed by Western Blotting with a rabbit polyclonal anti-Egfl7 antibody.

Figure 5:
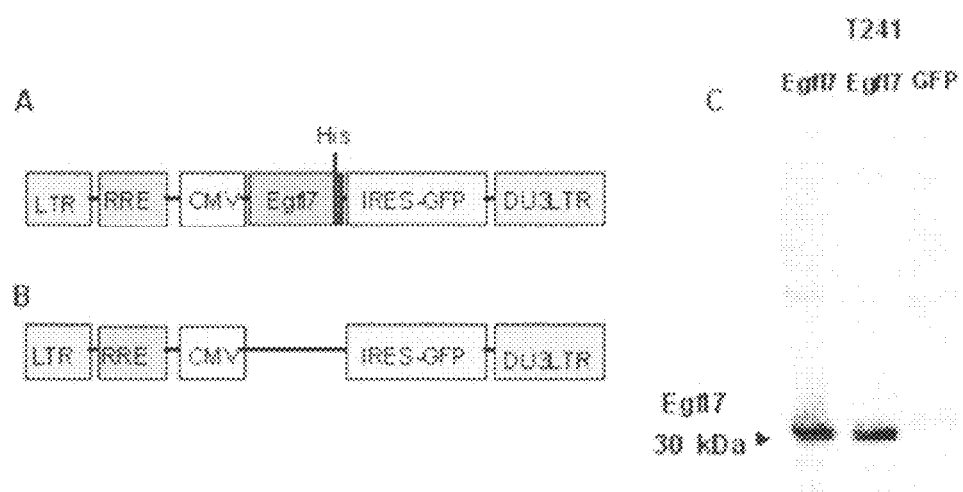
FIG. 5. Lentiviral transduction of tumor cell lines. The Egfl7 cDNA with a 6× Histidine tag was cloned downstream of the CMV promoter in the pHRST-IRES-GFP lentiviral construct (A). A control lentiviral construct with no insert was also created. (B) Overexpression of Egfl7 in GFP-sorted, lentivirus Egfl7-IRES-GFP transduced T241 cells demonstrated by (C, lanes labeled Egfl7) Western blotting of whole-cell extracts with a rabbit polyclonal anti-Egfl7 antibody.
Figure 6:
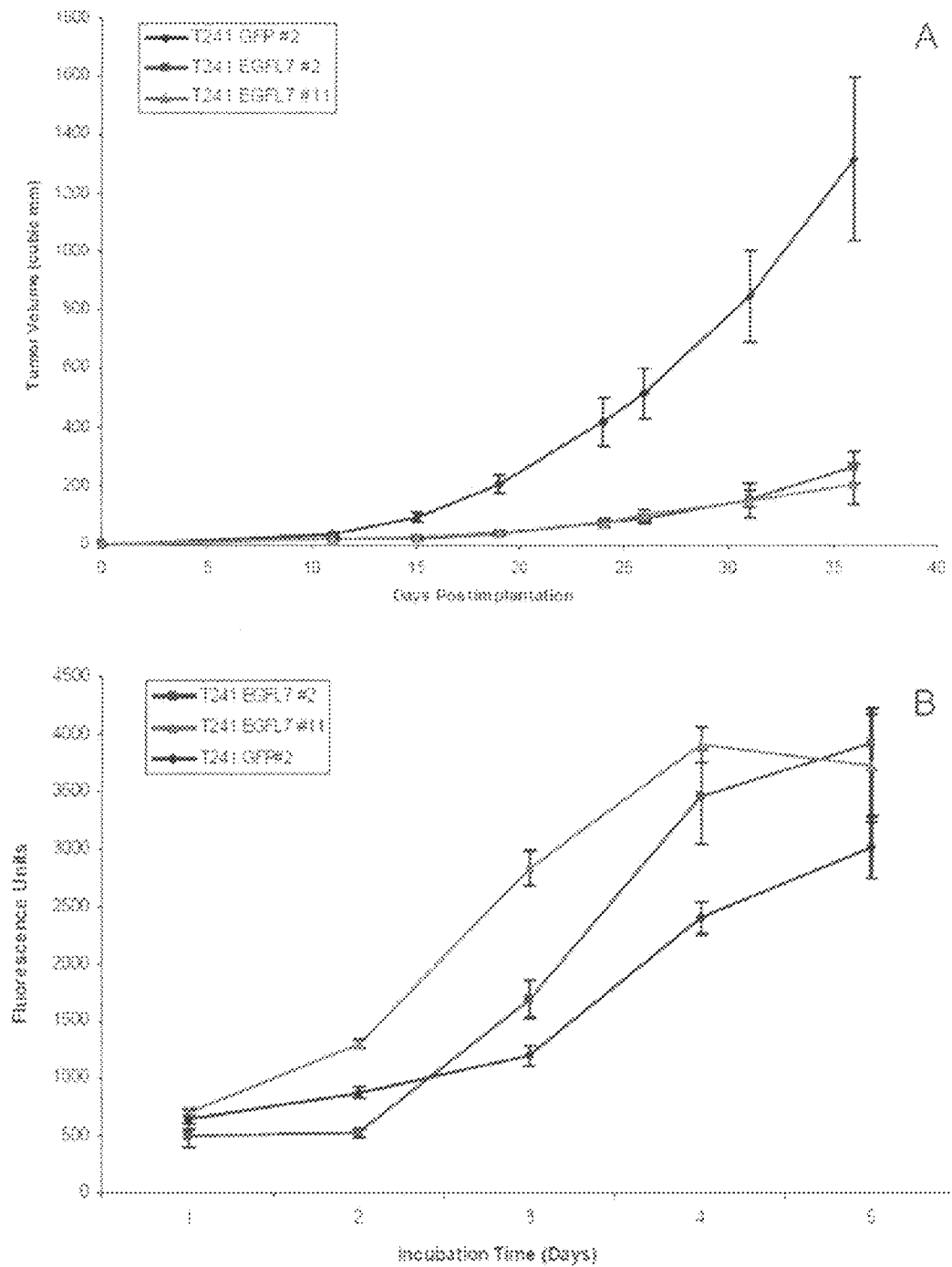
FIG. 6. Subcutaneous tumors formed by Egfl7 expressing T241 fibrosarcomas grow significantly slower than control GFP expressing tumors (Data points represent mean tumor volume ±S.E.M.) and are significantly smaller at the endpoint (p=0.001; p=0.014, Student's t-test). (A) In vitro comparisons of the rate of proliferation of Egfl7 expressing T241 cells to control GFP cells show that Egfl7 expression does not have an adverse affect on fibrosarcoma cell proliferation (Data points represent mean fluorescent unit of 3 wells ±S.E.M.). B. A comparison of the proliferation of Egfl7 expressing T241 cells to control GFP expressing cells reveals that Egfl7 expression does not adversely affect tumor cell proliferation.

Results:

Egfl7 Expressed by Lentiviral Transduced T241 Fibrosarcoma Cells. T241 fibrosarcoma cells transduced with lentiviruses encoding Egfl7 and control GFP were FACS sorted and expanded. Two T241 clones were isolated and shown to stably express Egfl7 in comparison to control cells transduced with a GFP lentivirus (FIG. 5C). A comparison of the proliferation of Egfl7 expressing T241 cells to control GFP expressing cells reveals that Egfl7 expression does not adversely affect tumor cell proliferation (FIG. 6B). In fact, cells expressing Egfl7 initially grow at a faster rate than GFP expressing cells although, at the endpoint of the experiment, there is no difference in cell number between Egfl7 expressing clones and the control GFP clone ($p=0.06$; $p=0.27$, Student's t-test) (FIG. 6B).

Subcutaneous tumors formed from both T241 clones expressing Egfl7 grow at a significantly slower rate and are unable to attain the same volume than control GFP expressing tumors ($p=0.001$; $p=0.014$, Student's t-test) (FIG. 6A). At the endpoint of the experiment, control GFP tumors had attained a mean volume of around 1300 cubic mm (n=6) while Egfl7 expressing tumors remained below a mean volume of 250 cubic mm (n=12). Due to the potent anti-angiogenic effect of adenoviral delivered Egfl7 from previous angiogenesis assays and the fact that Egfl7 expression does not adversely affect T241 cell proliferation in an autocrine manner, this remarkable inhibition of tumor growth in vivo is most likely due to a suppression of tumor angiogenesis.

Figure 7:
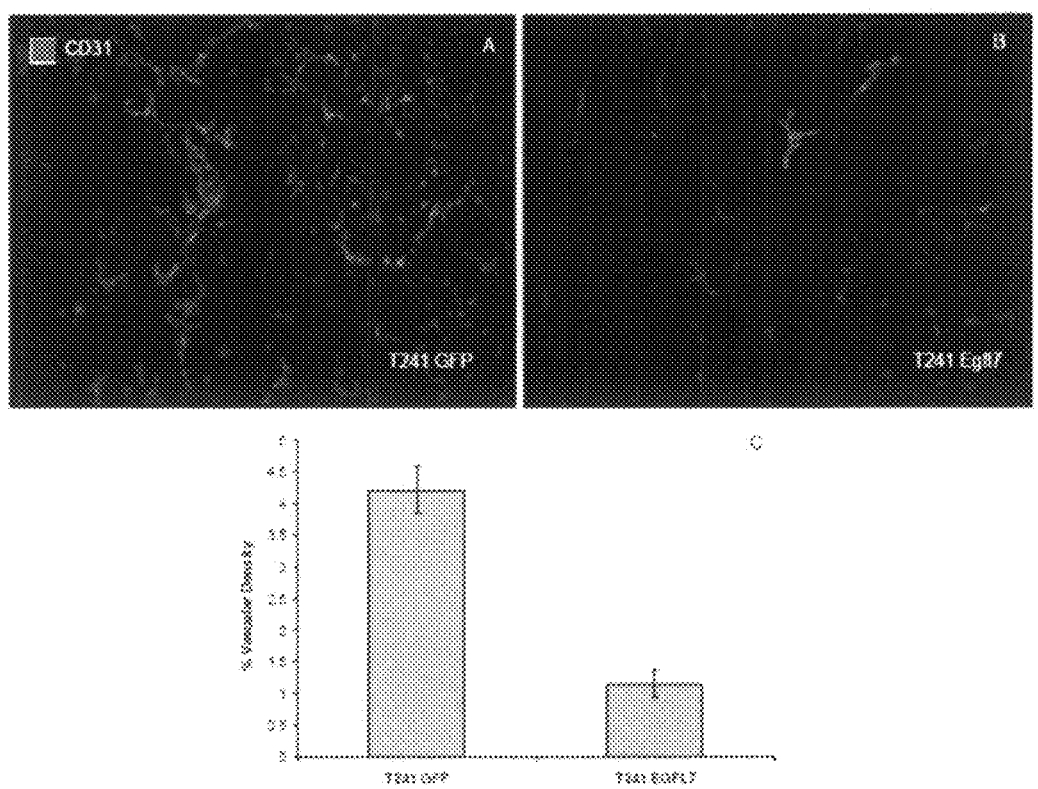
FIG. 7. Analysis of Tumor Vasculature. CD31 staining of size matched T241 tumors show a striking decrease in tumor vasculature in Egfl7 expressing T241 tumors (B) compared to control GFP tumors (A). (C) Quantitation of CD31 staining using Volocity reveals that the percent vascular density of size matched T241 Egfl7 tumors are significantly lower than that of T241 GFP tumors, p=0.001, Student's t-test (error bars represent ±S.E.M., bars represent the mean of n=10 pictures for T241 GFP and n=8 pictures for T241 Egfl7).
Figure 8:
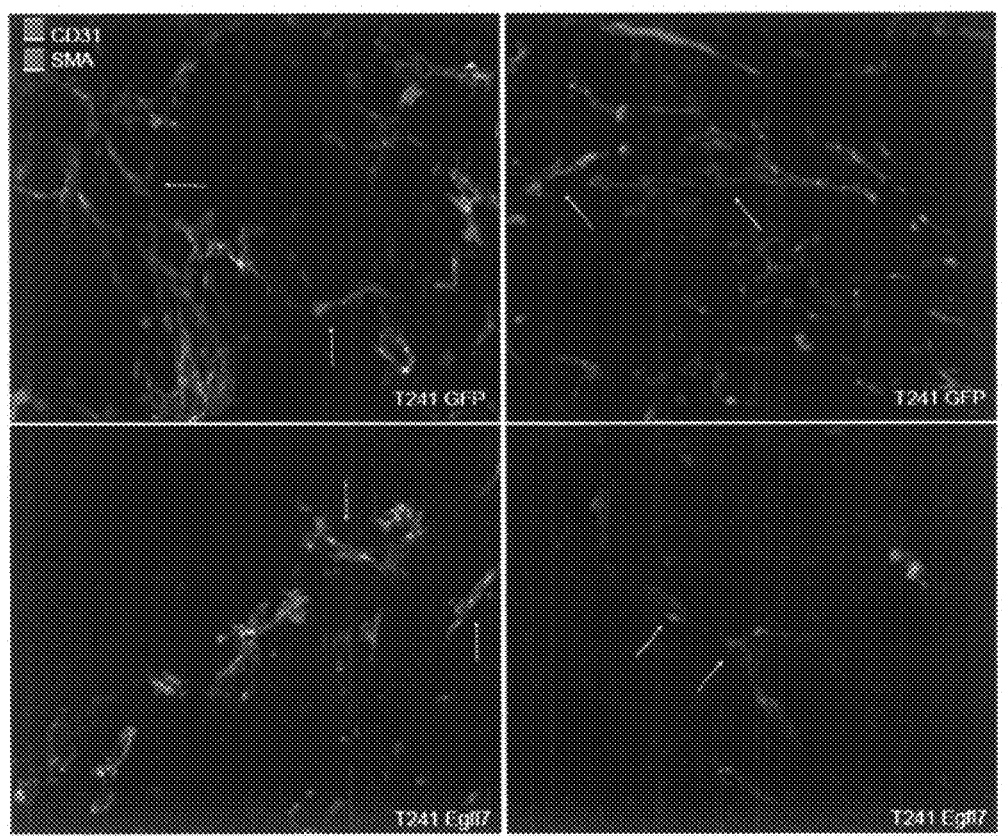
FIG. 8. Costaining of T241 subcutaneous tumors with FITC-CD31 and Cy3-SMA shows colocalization of pericytes and endothelial cells in Egfl7 expressing tumors. Control GFP expressing tumors show staining characteristic of aberrant tumor vasculature with poor association of pericytes with endothelial cells. White arrows indicate striking examples of intimate associations between pericytes (red) and endothelial cells (green) in an Egfl7 expressing tumor. Yellow arrows indicate pericytes detached from tumor vasculature.

Subcutaneous Tumors Expressing Egfl7 Show Reduced Vascularization. Size matched tumors from both Egfl7 expressing and GFP expressing tumors were harvested from perfused mice, sectioned, and stained with anti-CD31 FITC conjugated antibodies to visualize the vasculature. Tumor sections taken from control GFP expressing tumors show abundant CD31 staining (FIG. 7A) while sections from Egfl7 tumors have little to no positive CD31 staining (FIG. 7B). The percent vascular density of eight size matched GFP and Egfl7 expressing tumors was determined using Volocity to quantify the percent area density of CD31 staining as described. Egfl7 expressing tumors showed significantly lower percent vascular density ($p=0.001$, Student's t-test) than GFP expressing tumors (FIG. 7C). The striking decrease of tumor vasculature in Egfl7 expressing tumors further supports the hypothesis that Egfl7 is a powerful suppressor of tumor angiogenesis.

Endothelial Cells from Egfl7 Expressing Tumors Associate with Perivascular Cells. Pericytes, or perivascular cells, are multipotent support cells found in close association with endothelial cells of the microvasculature. The close spatial arrangement of perictyes and endothelial cells allows for communication between these cell types in the form of soluble factors and cell-cell contacts. In fact, the presence of closely attached pericytes is a hallmark of mature blood vessels. On the other hand, blood vessels formed through VEGF induced tumor angiogenesis are often characterized by a loose association or a complete absence of pericytes. This abnormality has been speculated to contribute to excessive vessel permeability caused by pathological VEGF activity.

Pericytes, visualized with a Cy3 conjugated anti-Smooth Muscle Actin antibody, in GFP expressing T241 subcutaneous tumors are detached from neighboring capillaries. In contrast, pericytes in Egfl7 expressing tumors colocalize closely with FITC-CD31 labeled endothelial cells, thereby implying that the vasculature in these tumors is more normalized. Normalization of tumor vasculature, exemplified by improved vessel integrity and the recruitment of supporting perivascular cells, is a general sign of VEGF blockade.

The Creation of Egfl7 Expressing Human Umbilical Vein Endothelial Cells. The potent anti-angiogenic and anti-tumor activity of Egfl7 and the normalizing effect of Egfl7 expression in vivo suggest that Egfl7 inhibits VEGF in an autocrine manner through inhibiting endothelial cell proliferation, migration, and/or tube formation. To test this hypothesis, the effect of Egfl7 on HUVECs was assayed in vitro. HUVECs were first transduced with Egfl7 lentivirus or GFP lentivirus to stimulate overexpression of Egfl7 as shown by Western blotting with a rabbit monoclonal anti-Egfl7 antibody (FIG. 6A). HUVECs that express the inserted gene could also be followed as GFP positive cells (FIG. 6B, C).

The angiogenic switch is a vital step in the development of macroscopic and metastatic tumors and is initiated by tumor secreted angiogenic activators, such as VEGF, that stimulate the proliferation, migration, and differentiation of neighboring endothelial cells. Egfl7 is an endothelial cell secreted protein. Due to the difficulty of obtaining significant amounts of purified Egfl7 protein, 6× Histidine tagged Egfl7 was overexpressed in T241 fibrosarcoma cells and implanted into adult mice. This method of expression ensures that Egfl7 is synthesized and posttranslationally modified within mammalian cells and is present in the local environment of the tumor mass where there is intimate contact between tumor cells and vascular endothelial cells. Expression of Egfl7 in this manner led to a striking decrease in vascularity and a potent inhibition of tumor growth in vivo, suggesting that Egfl7 restrains tumor growth by inhibiting VEGF induced tumor angiogenesis.

Vascular endothelial cells respond to angiogenic stimuli, in the form of VEGF or other soluble activators, by proliferating, migrating towards the source of chemoattractant, and differentiating into nascent vasculature. Therefore, the anti-angiogenic activity of Egfl7 in tumors could be due to attenuation of one or more of these three cellular responses. The effect of Egfl7 expression on endothelial cells was investigated in HUVECs transduced with lentiviruses encoding Egfl7 as described above. The results indicate that Egfl7 expression does not have a significant effect on HUVEC proliferation and tube formation, but may affect the ability of HUVECs to migrate towards VEGF as demonstrated in a transwell migration assay ($p=0.037$, Student's t-test). This implies that Egfl7's ability to inhibit tumor angiogenesis is due to a direct inhibition of endothelial cell migration towards VEGF.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reducing angiogenesis in an individual, the method comprising:

administering to an individual an effective dose of human or mouse Egfl7 polypeptide, wherein said administering provides for reduction of angiogenesis in the individual.

2. The method of claim 1, wherein said Egfl7 polypeptide reduces angiogenesis associated with a disorder selected from tumor growth, atherosclerosis, diabetic retinopathy, age-related maculopathy, and retrolental fibroplasia.

3. The method according to claim 1, wherein said Egfl7 polypeptide is human Egfl7.

4. The method of claim 1, wherein said administering is by a route selected from intravenous, in or around a solid tumor, systemic, intraarterial, intraocular, and topical.

* * * * *